United States Patent [19] [11] 4,053,589
Gans et al. [45] Oct. 11, 1977

[54] METHOD OF TREATING NUTRITIONAL DEFICIENCY DURING CARDIAC CACHEXIA, DIABETES, HYPOGLYCEMIA, GASTROENTEROLOGY, LIPID, CELL GLYCOGEN AND KERATIN-RELATED SKIN CONDITIONS AND ALCOHOLISM

[75] Inventors: Arnold M. Gans, Closter, N.J.; Alvin J. Goren, North Bergen, N.J.; Eli M. Gorenberg, Fair Lawn, N.J.

[73] Assignee: Control Drug Inc., Port Redding, N.J.

[21] Appl. No.: 698,353

[22] Filed: June 22, 1976

Related U.S. Application Data

[62] Division of Ser. No. 634,857, Nov. 24, 1975

[51] Int. Cl.² .................. A01N 9/20; A61K 37/00
[52] U.S. Cl. .................................. 424/177; 424/319
[58] Field of Search ........................... 424/319, 177

[56] References Cited

U.S. PATENT DOCUMENTS

| 3,698,912 | 10/1972 | Winitz | 424/319 |
| 3,701,666 | 10/1972 | Winitz | 424/319 |
| 3,920,838 | 11/1975 | Flatt et al. | 424/319 |
| 3,950,529 | 4/1976 | Fischer et al. | 424/319 |
| 4,003,992 | 1/1977 | Beigler | 424/101 |

*Primary Examiner*—Albert T. Meyers
*Assistant Examiner*—D. W. Robinson
*Attorney, Agent, or Firm*—Arthur A. Jacobs

[57] ABSTRACT

A method of treating nutritional deficiency during cardiac cachexia, diabetes, hypoglycemia, gastroenterology, skin conditions related to lipid, cell glycogen and keratin deficiencies and alcoholism which comprises ingestion of a pre-digested protein composition containing all of the essential amino acids and having a palatable taste and odor.

4 Claims, No Drawings

METHOD OF TREATING NUTRITIONAL DEFICIENCY DURING CARDIAC CACHEXIA, DIABETES, HYPOGLYCEMIA, GASTROENTEROLOGY, LIPID, CELL GLYCOGEN AND KERATIN-RELATED SKIN CONDITIONS AND ALCOHOLISM

This is a division of application Ser. No. 634,857, filed Nov. 24, 1975 and now allowed.

This invention relates to a method and composition for providing a highly efficient source of nutrition without undesirable side effects, and it especially relates to the provision of a source of protein in concentrated but highly palatable form.

One of the most significant aspects of the present invention is its utilization in the prevention of nutritional deficiency which is caused by disease or which is an undesirable condition in the treatment of a disease or surgical procedure.

The crucial effect in the body's response to nutritional deficiency or starvation is the preservation of the size and character of the body cell mass. The term "body cell mass" denotes the total mass of living, functioning, energy-exchanging, and mitotically active cells of the body comprising two large groups of tissues, namely skeletal muscle and visceral parenchyma.

Under conditions of disease, disuse or starvation, skeletal muscle shrinks markedly, reflecting a loss of protein from the body cell mass. A growing deficit in tissue protein may be detected and measured as negative nitrogen imbalance (less intake than excretion of protein nitrogen).

Nitrogen balance indicates that the rate of protein synthesis in the body equals that of protein degradation, since inactive nitrogen compounds are not stored in the body. The major changes in body cell mass during starvation are directed toward conserving proteins and maintaining body tissues as long as possible under the demands for energy fuel for vital functions. Outside the body cell mass are supportive fluids, including the plasma, lymph, and interstitial and transcellular fluids, as well as solids, including tendon, dermis, collagen, elastin, and fascia. In prolonged starvation, all of these substances begin to lose their integrity as the rate of protein breakdown rises above the rate of synthesis. Plasma proteins tend to maintain normal concentrations for some time after large amounts of protein are lost from the body cell mass; also, the synthesis of hemoglobin and albumin continues while muscle tissue generally is breaking down. Eventually, however, the onset of edema signals the loss of protein osmotic balance in the extracellular fluids.

Many diseases cause or are affected by loss of body mass, particularly the so-called "lean body mass" as distinguished from the fat mass which is contained mostly in adipose tissue as an accumulation of anhydrous neutral triglycerides. After these fats are used up for energy, the body begins to utilize the protein or lean body mass for energy purposes, causing destruction of vital body systems reflected by weight loss and anorexia. In surgery, this inhibits the process of tissue repair. Furthermore, it is recognized that loss of lean body mass parallels hypovolemia, or loss of the red cell mass, which creates a problem in surgical procedures.

An especially significant problem related to severe malnutrition is in cancer therapy. It has been found that significant advances in chemotherapy have produced an increase in the rates of cancer response and long-term survival in patients with most forms of malignant disease. The cachectic patient with cancer, however, exhibits a much narrower safe therapeutic margin for chemotherapy than does the well-nourished host in the early stages of metastatic disease, and malnutrition often eliminates these patients as candidates for adequate oncologic treatment. Common observations associated with most modes of cancer chemotherapy are weight loss, weakness, nausea, vomiting, and diarrhea. If these adverse side effects could be minimized, methods of treatment might be enhanced, greater destruction of cancer cells might be achieved, and the normal cell population might function optimally.

One theory correlating weight loss with cancer is that the cancerous tumor functions as a nitrogen trap and extracts amino acids for protein metabolism from the host's nitrogen pool, and because tumor anabolism exceeds catabolism, these amino acids are not recycled for use by the host. This theory is supported by the fact that a negative nitrogen balance is commonly found in cancer patients. Yet another theory is that there is a positive correlation between the extent of cancerous growth and the degree of hypoalbuminemia exhibited by the patient, whereby the presence of accelerated rates of albumin catabolism correspond to decreased levels of serum albumin. It has also been found that in chemotherapy and radiotherapy, the intestines suffer some damage to their absorbing cells.

In general, there has been continuing controversy on the extent to which the body wasting is attributable to reduced food intake due to loss of appetite, increased metabolic rate of the host, or preemption of available nutrients for general growth and maintenance of the tumor and irreversable damand by the tumor for specific essential nutrients. However, whichever theory is correct, the fact is that the patients must be made nutritionally replete not only to maintain the life system but to permit them to undergo such oncologic procedures as radiotherapy and chemotherapy, as well as surgery.

In order to overcome weight loss and anorexia, it has been proposed to use forced feeding, with a diet designed to be relatively normal in its distribution of protein, fat and carbohydrates. The diet was given either by mouth or by gastric tube. It was found, however, that this procedure was impractical because the patients were incapable of tolerating the forced feedings for any extended periods of time, complaining of uncomfortable fullness, accompanied, in some instances, by nausea or diarrhea. In addition, it was generally necessary to carry this procedure out in a hospital or similar institution.

Efforts have been made to overcome the above-noted problems by the use of a so-called "elemental diet," that is, one which is high in protein-building amino acids. One such "elemental diet" is a casein hydrolysate containing medium chain triglycerides. Although such elemental diets have been used with some success, they often suffer from the fact that not only do they contain a certain amount of triglycerides which form undesirable fats, but they are generally highly unpalatable, being characterized by a very bad taste and odor and/or nausea or diarrhea, so that they cannot be normally tolerated by the patient.

In recent years, the technique of intravenous hyperalimentation has been employed to provide parenteral nutritional support to depleted individuals. The substance used is a hypertonic glucose-amino acid solution that is administered by means of a catheter placed in a major central vein. Although this technique has produced some significant results in cancer patients undergoing chemotherapy and radiotherapy, it has various disadvantages. For example, it is a complex procedure that not only requires a high degree of skill but is unpleasant to the patient and a shock to his nervous system. Furthermore, it requires rigorous adherence to aseptic and antiseptic techniques in order to insure the sterility of the hyperalimentation solution and its delivery system, thereby, generally requiring treatment in a hospital or similar institution. In addition, it is a very costly procedure which places its long-term use beyond the financial ability of many patients.

In view of the many disadvantages of both the elemental diets and the hyperalimentation procedure, it has been necessary to search for another method of improving the nutritional status of patients suffering severe malnutrition with its consequent protein depletion. Such a method is embodied in the present invention.

In accordance with the present invention, an orally ingestible, predigested protein composition is used, which comprises a sweet-tasting and readily ingestible gelatin hydrolysate formulation containing all of the essential amino acids and being free of undesirable triglycerides and fats.

In its liquid form, the present invention comprises an aqueous composition preferably containing a gelatin hydrolysate, sorbitol, a palatable acid, such as citric acid, fumaric acid or adipic acid, for maintaining the necessary acid pH, tryptophane, a synthetic sweetener, and flavoring and coloring agents when desired. Preferably, one or more preservatives are included for stabilization purposes. The flavoring agent is one which is highly palatable and sweet, preferably cherry, orange, green apple, or the like, while the preservative agent may be any of a number of preservatives fit for human consumption, such as potassium sorbate, sodium benzoate, methyl parabem and propyl parabem, either alone or in admixture.

The gelatin hydrolysate used in the present invention is made by hydrolyzing animal collagen, preferably a collagen derived from the skin of pork bellies, by means of enzymatic hydrolysis, and then spray drying the gelatin solution. It is necessary to use enzymatic hydrolysis rather than acid or base hydrolysis because the enzyme converts the gelatin to the more palatable small peptides (i.e. mono-, di-, or tri-peptides) rather than to the more unpalatable amino acids. In addition, it produces fewer distasteful impurities.

The preferred enzymes used in the hydrolysis are those considered safe for human consumption. The most preferable are bromolin and papain, although other enzymes, such as pepsin and trypsin, may possibly be used.

The enzymatically hydrolyzed gelatins of the aforesaid type do not contain the essential amino acid tryptophane. Therefore, tryptophane is added to the composition in an amount to constitute from about 0.02 to about 0.75 parts by weight of the composition. Other adjustments in amino acid content may also be made for special purposes.

Although the gelatin hydrolysate of the present invention has a far better taste and odor than other gelatin hydrolysates, it does retain a certain amount of acridity. In the case of other gelatin products, it usually is necessary to add large amounts of sugar to at least partially mask the underlying acrid taste. In such instances, artificial sweeteners, such as sodium saccharin or the like, cannot readily be used because the aftertaste of these artificial sweeteners, when combined with the acrid taste of the gelatin product, would make the product relatively unpalatable.

In the present product, however, even though a certain small amount of residual acridity might remain, it is capable of being readily masked by the aforesaid artificial sweeteners, with no serious aftertaste problem except such as is normally present in the sweeteners themselves. Even this, however, is overcome by the inclusion of the sorbitol, which not only tastes sweet itself, but also acts to coat the palate and gullet surfaces with a lubricating effect so that the composition is permitted to slide easily into the stomach. In addition, the sorbitol coats the taste buds, further masking any possible residual acrid taste.

In the above manner, a product is produced which is a sugarless, lipid-free composition, that is free of those carbohydrates that effect rapid rise of blood glucose levels. In this respect, sorbitol, unlike sugar, only slowly affects the blood glucose.

The present invention is embodied in the following compositions:

In general, the liquid composition comprises the following range of proportions:

| Components | Parts by Wt. |
| --- | --- |
| hydrolyzed gelatin | 5 – 75 |
| tryptophane | 0.02 – 0.75 |
| acid | 0.3 – 10 |
| sorbitol (70%) | 7 – 25 |
| artificial sweetener (e.g. sodium saccharin) | 0.1 – 2 |
| lubricant (glycerine or the like) | 0.1 – 3 |
| preservatives | 0.4 – 1 |
| dye and flavor | 0 – 0.4 |
| water | 15 – 80 |

Three specific liquid formulas, having different concentrations of hydrolyzed gelatin, are shown in the following Table 1:

Table 1

| Components | Parts by Wt. (± 10% by wt.) | | |
| --- | --- | --- | --- |
| hydrolyzed gelatin | 5.0 | 47.0 | 72.0 |
| tryptophane | 0.02 | 0.2 | 0.3 |
| citric acid | 0.4 | 3.7 | 4.5 |
| sorbitol (70%) | 19.4 | 18.6 | 9.0 |
| artificial sweetener | 0.1 | 0.1 | 0.1 |
| glycerine | 0.1 | 1.1 | 0.1 |
| preservatives | 0.4 | 0.4 | 0.4 |
| dye and flavor | 0.04 | 0.1 | 0.15 |
| water | 77.0 | 30.0 | 16.0 |

The second formula of Table 1 is the preferred formula.

Illustrative of the procedure for making a liquid composition embodying the present invention is the following example:

EXAMPLE 1

400 lbs of water was charged into a stirrer-equipped electrically heated kettle and heated to 70° C, and then 9 lbs of l-tryptophane was added and dissolved in. The solution was then transferred to a (stirrer-equipped) 500 gallon holding tank.

Next the kettle was charged with 800 lbs of water, 2028 lbs of gelatin hydrolysate (powder), 160 lbs of citric acid and the mixture heated to 70° C with mixing continued until full solution resulted. The solution was thereafter added to the material already in the holding tank.

To the stirred mixture in the holding tank was added:

4½ lbs sodium benzoate dissolved in 24 lbs of water;
4½ lbs potassium sorbate dissolved in 24 lbs of water;
4½ lbs of methyl paraben and 2 lbs of propyl paraben dissolved in 50 lbs of glycerine;
102 g dye (#2 red) dissolved in 10 lbs of water; flavor (cherry) 2000 ml;
5 lbs of sodium saccharine dissolved in 20 lbs of water;
800 lbs of sorbitol (70% solution);
sufficient water to bring the volume to 500 gallons;

The above product comprises a liquid form of the composition.

Two tablespoonfuls (one ounce) of a typical gelatin hydrolysate made in the above manner has the following approximate composition (providing 15 gms. of soluble protein hydrolysate per 30 cc):

| Amino Acids | Mg. |
| --- | --- |
| L-Alanine | 1300 |
| L-Arginine | 1200 |
| L-Aspartic Acid | 900 |
| L-Cystine | 10 |
| L-Glutamic Acid | 1500 |
| Glycine | 3500 |
| L-Histidine | 110 |
| L-Hydroxyproline | 1000 |
| L-Leucine | 450 |
| L-Isoleucine | 200 |
| L-Lysine | 650 |
| Hydroxylysine | 150 |
| L-Methionine | 110 |
| L-Phenylalanine | 350 |
| L-Proline | 2300 |
| L-Serine | 1000 |
| L-Threonine | 300 |
| L-Tryptophane | 65 |
| L-Tyrosine | 100 |
| L-Valine | 350 |

The above content may vary somewhat from lot to lot.

A master formula for solid forms of the product (e.g. powders, granules, capsules and tablets) is shown in the following Table 2:

Table 2

| Components | Parts by Wt. |
| --- | --- |
| hydrolyzed gelatin | 5 – 75 |
| tryptophane | 0.2 – 0.5 |
| dispersent | 0.1 – 10.0 |
| artificial sweetener | 0.1 – 2 |
| dye and flavor | 0 – 2.0 |
| preservatives | 0.1 – 2.0 |
| lubricant (glycerine or the like) | 0.1 – 5.0 |
| soluble edible polymer | 0 – 5.0 |
| solid carrier | 5 – 100.0 |

The dispersent may be any of a number of materials such as, for example, corn starch, silica gel, etc.; the edible polymer may also be any of a number of materials such as, for example, PVP, methyl cellulose, etc.; the solid carrier may be any of a number of materials in perverulent (granular) form, such as, for example, dicalcium phosphate, mannitol, etc.; and the preservative may be any of a number of materials such as, for example, sodium benzoate, methyl paraben, etc.

The procedures for preparing the solid products are illustrated by the following:

EXAMPLE 2

(Master Mix)

Thoroughly blend the hydrolyzed gel, tryptophane, sweetener (e.g. sodium saccharin), dispersent and solid carrier. Then dissolve the preservative, polymer and any desired dye and flavor into a sufficient quantity of water, alcohol, mixtures of water and alcohol, or any other suitable solvent, to uniformly wet the powders. The blend is then mixed with the solution to form a wet powder. These steps are all generally performed at room temperature.

EXAMPLE 3

(Powders)

Dry the master mix of Example 2 at 25°–40° C and then pass the mixture through a No. 60 mesh screen.

EXAMPLE 4

(Capsules)

Add sufficient lubricant, such as magnesium stearate or talc, to the product of Example 3 and fill the total mixture into hard or soft gelatin capsules, using conventional capsule-filling equipment.

EXAMPLE 5

(Granules)

Pass the wet mass from Example 2 through a No. 8 to 16 mesh screen and then dry the granules at 25°–40° C.

EXAMPLE 6

(Tablets)

Add sufficient lubricant to the granules of Example 5 to effect a desirable slippage between the granules, and then compress the mixture in conventional tableting equipment to obtain a desirable weight and size.

The liquid or solid forms of the composition may also be used in gels, lozenges, candy bars, and the like. It is also possible to incorporate such compositions in suppositories by standard methods.

The liquid composition prepared in the manner disclosed in Example 1 above was used in a clinical study at the Whitestone General Hospital, Whitestone, N.Y. The study was carried out using twenty-five patients, twelve male and thirteen female, over a three-month period. Individuals exhibiting the following criteria were chosen: a loss in body mass to at least ten pounds below the ideal or usual body weight; a loss of appetite, fatigue, depression, on systemic cancer chemotherapy. The age range was twenty-three to seventy-four years and the patients represented a variety of advanced carcinomas. The patients studied included two groups, those treated as in-patients in the hospital, and those studied as out-patients in a clinical setting. All hospitalized patients were followed-up on an out-patient basis after discharge from the hospital.

Study Design For In-Patients

Twenty patients exhibiting the criteria were used in the study. Each patient was placed on a standard hospital diet supplemented, in most cases, with two fluid ounces of the composition three times a day, once at each meal. However, in order to accommodate the study to the individual needs of the patients, some exceptions to this design were made. In this respect, two individuals were given twelve fluid ounces of the composition daily, while another patient had her dosage decreased to three fluid ounces daily. Each patient was permitted to take the composition in that manner which best suited his or her taste. It was mixed with varying quantities of milk, fruit juices and carbonated beverages. All drinks were prepared daily and all ingredients measured with standard liquid measures.

All foods sent to patients were portion-controlled by use of standard liquid and dry measures and an ounce scale. A special ticket was placed on each tray at meal time so that upon return to the kitchen it was put aside until leftover foods were measured by the research assistant. A data sheet listing all foods eaten, calories, and gram intakes of protein, fat, and carbohydrate was maintained daily on each patient. Most food items were calculated by use of the diabetic exchange lists. However, for those items that were not calculatable by this short method, the following were referred to: Bowes & Church *Food Values of Portions Commonly Used*, Tenth Edition; U.S. Department of Agriculture *Composition of Foods* (Handbook No. 8 ); Table A-1 of Robinson's *Normal and Therapeutic Nutrition*, Fourteenth Edition. All patients were subject to complete blood and platelet counts every other day, and an S.M.A.-12 weekly.

Study Design For Out-Patients

The out-patient procedure applied to all hospitalized patients after discharge and to five individuals who were treated only in this capacity. The out-patients were seen at the hospital clinic or at a private office once a week, with two exceptions. All patients were instructed to take two fluid ounces of the composition three times daily, once at each meal; however, as with the hospitalized patients, the amount was increased or decreased for certain individuals to meet their personal need. All patients were asked to record the amount of the composition taken daily. The patient's weight was taken and recorded during each weekly visit and a blood count and S.M.A.-12 were also taken.

The procedure outlined was followed by all out-patients, with the aforesaid two exceptions. These two individuals, indicated in the following table as L. B. and J. C., were hospitalized for 47 and 38 days respectively. After discharge, both patients returned to their homes. J. C. returned to the clinic for one visit and L. B. is expected to return within one or two months for further hospitalization. Both individuals received their supplies of the composition by mail and sent their daily weights and intakes of the composition to the hospital.

The results of the above study are tabulrted in the following table, the term "Weight Before" meaning the patient's weight preceeding the dosage period described above, the term "On" meaning the patient's weight during the dosage period, and the term "After" meaning the period completion of the dosage period:

| | | | \multicolumn{3}{c|}{Weight Before} | | \multicolumn{4}{c|}{On} | \multicolumn{3}{c|}{After} |
|---|---|---|---|---|---|---|---|---|---|---|---|---|---|
| Subject | Age/Sex | Cancer | 1 year before | Just before | Gain (+) Loss (−) lbs/1 yr. | Dosage oz/day | Wt. Before | Time Days | Wt. After | Gain (+) Loss (−) lbs. | Time Days | Wt. After | Gain (+) Loss (−) lbs. |
| JC | 48/F | breast | no data | 165 | | 6 oz. | 157 | 50 | 165 | +8 | | | |
| JB | 72/M | colon | 190 | 160½ | −29 ½ | 6 oz. | 160½ | 8 | 164 | +3½ | | | |
| " | " | " | | | | 6 oz. | 165½ | 5 | 168 | +2½ | | | |
| FW | 67/M | lung | 170 | 147 | −23 | 6 oz. | 147 | 10 | 151½ | +4½ | 30 | 149 | −3½ |
| MC | 70/M | colon | 150 | 125 | −25 | 6 oz. | 125 | 35 | 131 | +6 | | | |
| JD | 53/M | rectum | 145 | 118 | −27 | 6 oz. | 114 | 17 | 130 | +16 | | | |
| DA | 62/F | breast | 145 | 123 | −22 | 2-3 oz. | 123 | 24 | 130½ | +7½ | 18 | 129 | −1½ |
| AR | 74/M | colon | 155 | 110 | −45 | 0 | — | — | | | | | |
| LB | 55/M | | 172 | 158½ | −13½ | 6-12 oz. | 158½ | 30 | 164 | +5½ | 11 | 161 | −3 |
| CB | 48/M | lung | 165 | 142 | −23 | 6 oz. | 142 | 13 | 149 | +7 | | | |
| CP | 52/F | breast | 99 | 89 | −10 | 6 oz. | 89 | 22 | 93 | +4 | 30 | 86 | −7 |
| NM | 33/F | uterus | 97 | 89 | − 8 | 6 oz. | 89 | 9 | 95 | +6 | 8 | 92 | −3 |
| AY | 63/F | sinus | 110 | 93 | −17 | 4 oz. | 93 | 14 | 99 | +6 | 7 | 90 | −9 |
| TM | | rectum | 170 | 138 | −32 | 6 oz. | 138 | 21 | 143 | +5 | | | |
| AZ | 60/M | myeloma | 155 | 140 | −15 | 6 oz. | 140 | 40 | 157 | +17 | | | |
| RS | 66/F | lympho sarcoma | 138 | 103 | −35 | 6 oz. | 103 | 9 | 106 | +3 | | | |
| DS | 22/M | Hoshkin | 135 | 115 | −20 | 6-12 oz. | 115 | 48 | 127 | +12 | | | |
| VS | 55/F | breast | 155 | 138 | −17 | 6 oz. | 138 | 22 | 154 | +16 | | | |
| AL | 74/F | breast | 155 | 129 | −26 | 6 oz. | 129 | 26 | 131 | +2 | | | |
| EP | 64/F | uterus | 117 | 105½ | −11½ | 6 oz. | 106½ | 5 | 111½ | +5 | | | |
| RW | 54/M | bladder | | 120 | | 3 oz. | 120 | 10 | 128 | +8 | | | |
| AG | | | | 145½ | | ? | 145½ | 3 | 148½ | +3 | | | |
| EW | 38/F | uterus | 161 | 135 | −26 | ? | 135 | 90 | 135 | 0 | | | |
| DP | | sarcoma | 170 | 138 | −32 | ? | 138 | 60 | 150 | +12 | | | |
| ET | | | 148 | 146½ | −1½ | 6 oz. | 146½ | 40 | 152¾ | +6¼ | 20 | 142 | −10¾ |

INFLUENCE OF PREDIGESTED PROTEIN PRODUCT ON THE WEIGHT OF CANCER PATIENTS

The results of the study as indicated in the preceeding table clearly show the startling weight gains resulting from the use of the present composition.

The present invention is not only clearly valuable in the treatment of patients undergoing surgery or cancer therapy but in many other instances where nutritional deficiency is a serious obstacle to treatment or recovery such as cardiac cachexia, diabetes, hypoglycemia, gastroenterology, alcoholism, and the like. Furthermore, the invention is valuable not only in disease-related conditions but in many other situations where body build-up in a relatively rapid and efficient manner is desired. In this respect, it may be used to provide weight-gain for ingerently thin or run-down persons, without the addition of excess fats. It may also be used by athletes to build up their lean body mass and by persons under stress who cannot tolerate large amounts of bulk food. It is also useful in skin disorders related to lipid, cell glycogen or keratin deficiencies since it provides a nutritionally satisfactory diet without fats and oils and improves the formation of keratin by amino acid supplementation.

The present composition may also be used to prevent obesity since the substitution of the fat-free and low carbohydrate composition for other foods provides sufficient nutrition without unduly raising the fat and lipid level.

The particular dosage used may vary somewhat in accordance with the particular subject, his or her physiological or psychological condition and the disease or therapy involved. However, the particular dosage to be prescribed would be well within the skill of the treating physician or others skilled in the art, or even of the user himself in those instances not requiring the supervision of a physician or other person of special skill.

Although the use of an artificial sweetener such as sodium saccharin has been described above, and this is the preferable type of sweetener for these compositions, it is possible to substitute sugar or mixtures of sugar and artificial sweeteners for use in those instances where the ingestion of carbohydrates or carbohydrate-forming materials is not a problem. It is also possible to substitute other carbohydrates with varying caloric or insulin or blood-glucose stimulating activity.

The invention claimed is:

1. A method of treating nutritional deficiency during cardiac cachexia, diabetes, hypoglycemia, gastroenterology, skin conditions related to lipid, cell glycogen and keratin deficiencies, and alcoholism which comprises administering by ingestion to a patient having such a deficiency a nutritionally effective amount of a composition comprising about 5 to about 75 parts by weight of hydrolyzed gelatin, about 0.02 to about 0.75 parts by weight of tryptophane, about 0.1 to about 2 parts by weight of a sweetener, and about 5 to about 100 parts by weight of an ingestible carrier, said nutritional composition containing essentially the following amino acids in parts by weight: about 13 parts L-alanine, about 12 parts L-arginine, about 9 parts L-aspartic acid, about 0.1 parts L-cystine, about 15 parts L-glutamic acid, about 35 parts glycine, about 1.1 parts L-histidine, about 10 parts L-hydroxyproline, about 4.5 parts L-leucine, about 2 parts L-isoleucine, about 6.5 parts L-lysine, about 1.5 parts hydroxylysine, about 1.1 parts L-methionine, about 3.5 parts L-phenylalanine, about 23 parts L-proline, about 10 parts L-serine, about 3 parts L-threonine, about 0.65 parts L-tryptophane, about 1 part L-tyrosine, and about 3.5 parts L-valine.

2. The method of claim 1 wherein said hydrolyzed gelatin is a product formed by the enzymatic hydrolysis of animal collagen.

3. The method of claim 1 wherein the composition is in liquid form and wherein the carrier is water in a proportion of about 15 to 80 parts by weight, said composition additionally including about 0.3 to 10 parts by weight of a palatable acid, about 7 to 25 parts by weight of sorbitol (70%), about 0.1 to 3 parts by weight of a preservative, and about 0 – 0.4 parts by weight of a dye and flavoring agents.

4. The method of claim 1 wherein the composition is in solid form and wherein the carrier is a pulverulent solid in a proportion of about 5 to 100 parts by weight, said composition additionally including about 0.1 to 10 parts by weight of a dispersent, about 0 to 2 parts by weight of dye and flavoring agents, about 0.1 to 2 parts by weight of a preservative, about 0.1 to 5 parts by weight of a lubricant, and about 0 to 5 parts by weight of a soluble edible polymer.

* * * * *